United States Patent [19]

Inoue et al.

[11] Patent Number: 5,631,338
[45] Date of Patent: May 20, 1997

[54] PROCESS FOR PREPARING BISPHENOL A

[75] Inventors: Kaoru Inoue; Tuneyuki Ohkubo; Takashi Terajima, all of Yokohama, Japan

[73] Assignee: Mitsui Toatsu Chemicals, Inc., Tokyo, Japan

[21] Appl. No.: 499,904

[22] Filed: Jul. 11, 1995

[30] Foreign Application Priority Data

Jul. 21, 1994 [JP] Japan .................................. 6-169664
Dec. 1, 1994 [JP] Japan .................................. 6-298405

[51] Int. Cl.$^6$ .................................................. C08G 77/28
[52] U.S. Cl. .......................... 528/30; 556/428; 556/429; 568/727
[58] Field of Search ............................ 568/727; 528/30; 556/428, 429

[56] References Cited

U.S. PATENT DOCUMENTS

| | | | |
|---|---|---|---|
| 3,496,239 | 2/1970 | Hamilton et al. | 568/727 |
| 4,045,379 | 8/1977 | Kwantes et al. | 568/727 |
| 4,191,843 | 3/1980 | Kwantes et al. | 568/727 |
| 4,294,995 | 10/1981 | Faler et al. | |
| 4,859,803 | 8/1989 | Shaw | 568/727 |
| 5,075,511 | 12/1991 | Li | 568/727 |
| 5,463,140 | 10/1995 | Wehmeyer et al. | 568/727 |

FOREIGN PATENT DOCUMENTS

| | | |
|---|---|---|
| 0293852 | 12/1988 | European Pat. Off. . |
| 937072 | 10/1959 | United Kingdom . |
| 1183564 | 3/1970 | United Kingdom . |
| 1185102 | 3/1970 | United Kingdom . |
| 1185223 | 3/1970 | United Kingdom . |
| 1539186 | 1/1979 | United Kingdom . |

OTHER PUBLICATIONS

Patent Abstracts of Japan, vol. 018, No. 236, (C–1196), May 6, 1994, JP-A-08 025420, Feb. 1994—*Abstract*.

*Primary Examiner*—Ralph H. Dean
*Attorney, Agent, or Firm*—Burns, Doane, Swecker & Mathis

[57] ABSTRACT

The present invention provides a process for preparing bisphenol A with a high conversion and selectivity by reacting phenol with acetone in the presence of both a polyorganosiloxane having a mercapto group-containing hydrocarbon group and an acid. It is preferable that the polyorganosiloxane having a mercapto group-containing hydrocarbon group and the acid is a polyorganosiloxane having both a mercapto group-containing hydrocarbon group and a sulfonic acid group.

14 Claims, No Drawings

PROCESS FOR PREPARING BISPHENOL A

BACKGROUND OF THE INVENTION

1. Field of the Invention

The present invention relates to a process for preparing 2,2-bis(4'-hydroxyphenyl)propane (hereinafter referred to as bisphenol A) through dehydration-condensation of phenol and acetone.

Bisphenol A is an extremely useful compound for industrial purposes and is generally used as an important material for the production of polycarbonates, polyesters, epoxy resins, and developers of heat-sensitive paper. Bisphenol-A applied to polycarbonate resins is required to be colorless and of high purity.

2. Description of the Related Art

Bisphenol A is typically prepared by dehydration-condensation of two molecules of phenol and one molecule of acetone in the presence of an acid catalyst like hydrochloric acid.

When the reaction is carried out at a relatively low temperature using hydrochloric acid as a homogeneous catalyst, it proceeds with crystallization of an adduct of phenol with bisphenol A, thereby giving bisphenol A with a high conversion of acetone and a high 4,4'-selectivity. The homogeneous acid catalyst like hydrochloric acid, however, requires removal of the catalyst from a reaction mixture or neutralization of the reaction mixture. Therefore, the process is so complicated as to consume much time and labor. Homogeneous dissolution of the acid in the reaction solution further causes corrosion of equipment used in the reaction. Reaction vessels should be made of rather expensive, anti-corrosive materials accordingly.

In view of such circumstances, solid heterogeneous catalysts have increasingly been applied to the industrial preparation of bisphenol A.

Known examples of solid heterogeneous catalysts include zeolites, salts of heteropolyacids partially neutralized and insolubilized, and strongly acidic cation exchange resins. These solid heterogeneous catalysts, however, have relatively low catalytic activity and selectivity.

A method applicable to overcome the low performance of these solid catalysts is to add a sulfur-containing compound as a cocatalyst together with an acid catalyst to the reaction system. It is known that addition of such cocatalyst enhances the catalytic activity and reaction selectivity.

Known sulfur-containing compounds exerting the enhancement effect are thiol compounds like alkylmercaptan and benzylmercaptan. These compounds are homogeneously dissolved in the reaction system to enhance the activity of the acid catalyst and realize the high 4,4'-selectivity of bisphenol A, but they cause the problem of purification of the final product or bisphenol A; that is, bisphenol A should be separated from these cocatalysts like the homogeneous acid catalyst described above.

Several methods have been proposed to fix these thiol compounds and to prevent contamination of the final product with the thiol compounds. A method disclosed in Japanese Patent Publication No. 37-14721, for example, esterifies a mercaptoalkyl alcohol with part of acidic groups of a strongly acidic cation exchange resin and fixes the mercapto compound to the cation exchange resin through the ester linkage. Another method disclosed in Japanese Patent Publication No. 46-19953 partially neutralizes a strongly acidic cation exchange resin with a mercaptoalkylamine to fix the mercapto compound. A method disclosed in Japanese Patent Laid-open No. 52-19189 partially neutralizes a strongly acidic cation exchange resin with a cyclic mercaptoamine to fix the mercapto compound through ionic bonding. Another method disclosed in U.K. Patent No. 1539186 fixes a mercaptoamino acid through ionic bonding with a cation exchange resin. The catalysts prepared by fixing mercapto compounds to ion exchange resins, however, easily deteriorate due to the low heat resistance of the ion exchange resins. Mercapto compounds fixed by the above processes are thermally unstable and easily decomposed and liberated. This results in similar drawbacks of the homogeneous acid catalysts and homogeneous mercapto compounds described above. The fixation is attained by the reaction of the mercapto compounds described above with acid groups which can effectively work as reaction catalyst, thereby decreasing the quantity of effective acid.

SUMMARY OF THE INVENTION

The inventors have noted the fact that in preparation of bisphenol A through dehydration-condensation of phenol and acetone in the presence of an acid catalyst, a mercapto compound working as a cocatalyst enhances the reaction activity and selectivity. As a result of extensive studies to overcome the problems of separation and purification in the conventional homogeneous system of a mercapto compound and unstablility in the fixation of a mercapto compound, the inventors have found that a polyorganosiloxane obtained by fixing an organic mercaptan compound in a siloxane matrix is favorably applicable as the mercapto compound added as a cocatalyst in the process of preparation of bisphenol A through dehydration-condensation of phenol and acetone in the presence of an acid catalyst. This cocatalyst is thermally stable and effectively suppresses the elimination and liberation of mercapto groups even under high-temperature conditions and remarkably enhances the reaction activity and selectivity of the catalyst. The inventors have also noted the advantages of heterogeneous acid catalysts in the reaction process and have found that a polyorganosiloxane obtained by fixing both an acid group like a sulfonic acid group and a mercapto group-containing hydrocarbon group in a siloxane matrix gives a thermally stable heterogeneous catalyst having high activity and selectivity, wherein a cocatalyst component and an acid catalyst component are simultaneously fixed.

The present invention applies a mercapto group-containing polyorganosiloxane as a cocatalyst, as well as an acid catalyst. This effectively prevents the reaction product from being contaminated with the mercapto group even when the dehydration-condensation process is executed under high-temperature conditions. The cocatalyst applied does not lower the cocatalytic effect but maintains its performance over a long period of time in the preparation of bisphenol A.

A polyorganosiloxane having both a sulfonic acid group and a mercapto group-containing hydrocarbon group gives a stable heterogeneous catalyst. Neither the acid catalyst component nor the cocatalyst component is eliminated or liberated. This catalyst does not lower its catalytic activity in the dehydration-condensation process and allows bisphenol A to be manufactured economically, and the catalyst is easily separated after the reaction.

One object of the present invention is thus to provide a method of manufacturing bisphenol A in high yield and selectivity through dehydration-condensation of phenol and acetone in the presence of an acid catalyst, where the final product or bisphenol A is not contaminated with a mercapto compound and the mercapto compound is not decomposed or liberated even under the high-temperature conditions.

Another object of the present invention is to provide a novel solid catalyst, which is obtained in high efficiency by the simultaneous fixation of an acid catalyst and a mercapto group. The catalyst is easily separable and recoverable from the reaction product and is effective for industrial purposes.

According to the method of the invention:

(1) bisphenol A can be prepared through dehydration-condensation of acetone and phenol in high yield and selectivity; and (2) the industrially important material, bisphenol A can be preferentially manufactured from safety, process efficiency, and economical viewpoints.

DETAILED DESCRIPTION OF THE INVENTION

The present invention provides a process for manufacturing bisphenol A through the dehydration-condensation of phenol and acetone in the presence of an acid and a polyorganosiloxane having a mercapto group-containing hydrocarbon group. The invention also provides a process for manufacturing bisphenol A in the presence of a polyorganosiloxane having both a sulfonic acid group and a mercapto group-containing hydrocarbon group.

According to another aspect, the present invention is directed to a polyorganosiloxane having a sulfonic acid group and a mercapto group-containing hydrocarbon group, which is obtainable by the following steps of:

hydrolyzing at least one silane compound expressed by the general formula of $X_nSi(R_1)_{4-n}$ to yield a polyorganosiloxane, wherein n is an integer of from 1 to 3; X is at least one selected from the group consisting of a chlorine atom, a bromine atom, an iodine atom, and an alkoxyl group; $R_1$ is at least one hydrocarbon group selected from the group consisting of 1 to 20 carbon atoms-containing hydrocarbon groups having at least one mercapto group (—SH), 6 to 20 carbon atoms-containing hydrocarbon groups having an aromatic group, 1 to 15 carbon atoms-containing alkyl groups having at least one halogen atom, 2 to 15 carbon atoms-containing olefinic hydrocarbon groups having at least one carbon-carbon unsaturated double bond, and 2 to 15 carbon atoms-containing hydrocarbon groups having at least one epoxy group; and Si represents a silicon atom;

sulfonating the hydrocarbon group $R_1$ to yield a polyorganosiloxane having a sulfonic acid group;

silylating the sulfonic acid group-containing polyorganosiloxane with at least one silane compound expressed by the general formula of $X_nSi(R_2)_{4-n}$, wherein n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom; and hydrolyzing the silylated polyorganosiloxane.

The present invention is also directed to a polyorganosiloxane having a sulfonic acid group and a mercapto group-containing hydrocarbon group, which is obtainable by the following steps of:

silylating silica gel with at least one silane compound expressed by the general formula of $X_nSi(R_1)_{4-n}$ and hydrolyzing the silylated compound to yield a polyorganosiloxane, wherein n is an integer of from 1 to 3; X is at least one selected from the group consisting of a chlorine atom, a bromine atom, an iodine atom, and an alkoxyl group; $R_1$ is at least one hydrocarbon group selected from the group consisting of 1 to 20 carbon atoms-containing hydrocarbon groups having at least one mercapto group (—SH), 6 to 20 carbon atoms-containing hydrocarbon groups having an aromatic group, 1 to 15 carbon atoms-containing alkyl groups having at least one halogen atom, 2 to 15 carbon atoms-containing olefinic hydrocarbon groups having at least one carbon-carbon unsaturated double bond, and 2 to 15 carbon atoms-containing hydrocarbon groups having at least one epoxy group; and Si represents a silicon atom;

sulfonating the polyorganosiloxane to yield a polyorganosiloxane having a sulfonic acid group;

silylating the sulfonic acid group-containing polyorganosiloxane with at least one silane compound expressed by the general formula of $X_nSi(R_2)_{4-n}$, wherein n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom; and hydrolyzing the silylated polyorganosiloxane.

According to another aspect, the present invention is directed to a process for preparing a polyorganosiloxane having a sulfonic acid group and a mercapto group-containing hydrocarbon group, which includes the following steps of:

hydrolyzing at least one silane compound expressed by the general formula of $X_nSi(R_1)_{4-n}$ to yield a polyorganosiloxane, wherein n is an integer of from 1 to 3; X is at least one selected from the group consisting of a chlorine atom, a bromine atom, an iodine atom, and an alkoxyl group; $R_1$ is at least one hydrocarbon group selected from the group consisting of 1 to 20 carbon atoms-containing hydrocarbon groups having at least one mercapto group (—SH), 6 to 20 carbon atoms-containing hydrocarbon groups having an aromatic group, 1 to 15 carbon atoms-containing alkyl groups having at least one halogen atom, 2 to 15 carbon atoms-containing olefinic hydrocarbon groups having at least one carbon-carbon unsaturated double bond, and 2 to 15 carbon atoms-containing hydrocarbon groups having at least one epoxy group; and Si represents a silicon atom; and sulfonating the hydrocarbon group $R_1$ to yield a polyorganosiloxane having a sulfonic acid group;

silylating the sulfonic acid group-containing polyorganosiloxane with at least one silane compound expressed by the general formula of $X_nSi(R_2)_{4-n}$, wherein n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom; and hydrolyzing the silylated polyorganosiloxane.

The present invention also provides a process for preparing a polyorganosiloxane having a sulfonic acid group and a mercapto group-containing hydrocarbon group, which includes the following steps of:

silylating silica gel with at least one silane compound expressed by the general formula of $X_nSi(R_1)_{4-n}$ and hydrolyzing the silylated compound to yield a polyorganosiloxane, wherein n is an integer of from 1 to 3; X is at least one selected from the group consisting of a chlorine atom, a bromine atom, an iodine atom, and an alkoxyl group; $R_1$ is at least one hydrocarbon group selected from the group consisting of 1 to 20 carbon atoms-containing hydrocarbon groups having at least one mercapto group (—SH), 6 to 20 carbon atoms-containing hydrocarbon groups having an aromatic group, 1 to 15 carbon atoms-containing alkyl groups having at least one halogen atom, 2 to 15 carbon atoms-containing olefinic hydrocarbon groups having at least one carbon-carbon unsaturated double bond, and 2 to 15 carbon atoms-containing hydrocarbon groups having at least one epoxy group; and Si represents a silicon atom;

sulfonating the polyorganosiloxane to yield a polyorganosiloxane having a sulfonic acid group;

silylating the sulfonic acid group-containing polyorganosiloxane with at least one silane compound expressed by the general formula of $X_nSi(R_2)_{4-n}$, wherein n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom; and hydrolyzing the silylated polyorganosiloxane.

The essential features of the invention are further described in detail.

Purification is generally not required for phenol or acetone used in the present invention. Although the purity of phenol and acetone is not restricted, either industrial grade or general reagent grade is preferable. Phenol and acetone may be diluted with a reaction-inactive medium, such as a saturated hydrocarbon.

The acid catalyst applied to the present invention is not restricted and may be any acid having dehydration-condensation activities, such as protonic acids and Lewis acids. Both homogeneous acid catalysts which are dissolved homogeneously in the reaction system and heterogeneous acid catalysts which exist as solid in the reaction system are applicable to the present invention. Heterogeneous acid catalysts are, however, preferable for easy separation of the catalyst from the reaction product. It is further preferable that the acid catalyst has a high heat resistance.

Concrete examples of the heterogeneous acid catalyst applicable to the invention include partially neutralized heteropolyacids, which are obtained by substituting part of protons in a heteropolyacid by alkali metal ions or ammonium ions to form a heterogeneous solid, heteropolyacids and their salts held on a carrier such as active carbon, alumina, silica and diatomaceous earth, zeolites and layered clay compound. The acid catalyst used in the present invention is, however, not restricted to such heterogeneous acid catalysts, and may be another solid acid catalyst or a homogeneous acid catalyst.

The process for the present invention uses a polyorganosiloxane having a mercapto group-containing hydrocarbon group as a cocatalyst, together with the acid catalyst.

It is preferable to use a polyorganosiloxane obtainable by simultaneously fixing an acid and a cocatalyst, mercapto group-containing hydrocarbon group, to a polyorganosiloxane. Especially preferable is a polyorganosiloxane having both a sulfonic acid group and a mercapto group-containing hydrocarbon group.

The polyorganosiloxane having a mercapto group-containing hydrocarbon group used in the present invention has a structure that mercapto-containing hydrocarbon groups are bonded directly to silicon atoms in a siloxane matrix of siloxane linkage through carbon-silicon bonding.

In such polyorganosiloxanes, on average, 0.05 to 3, preferably 0.1 to 2, more preferably 0.2 to 1 mercapto group-containing hydrocarbon groups are bonded to one silicon atom of siloxane structure through the carbon-silicon bonding.

All the hydrocarbon groups or only part of the hydrocarbon groups may contain one or more mercapto groups, particularly the former type is preferable. The polyorganosiloxane having a mercapto group-containing hydrocarbon group used in the present invention is not restricted in any way by the quantity of mercapto groups.

The polyorganosiloxane having a mercapto group-containing hydrocarbon group used as a cocatalyst in the present invention may be prepared according to one of the following methods, however, the invention is not restricted to the methods of preparation described below.

An easily available method is hydrolyzing a silane compound expressed by the general formula of $X_nSi(R_2)_{4-n}$, wherein n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom.

Another possible method is hydrolyzing a mixture of the above silane compound and at least one silane compound expressed by the general formula of $SiX_4$, wherein X is at least one selected from the group consisting of a chlorine atom, a bromine atom, an iodine atom, and an alkoxyl group; and Si represents a silicon atom.

The process for the present invention applies the polyorganosiloxane having a mercapto group-containing hydrocarbon group prepared as above to the reaction as a cocatalyst, together with an acid catalyst.

A polyorganosiloxane having both a sulfonic acid group and a mercapto group-containing hydrocarbon group, which is obtainable by fixing sulfonic acid in the polyorganosiloxane having a mercapto group-containing hydrocarbon group, can be used effectively as a heterogeneous catalyst fixed as a cocatalyst in the process for the present invention.

The polyorganosiloxane having both a sulfonic acid group and a mercapto group-containing hydrocarbon group used in the present invention has a structure that sulfonic acid group-containing hydrocarbon groups and mercapto-containing hydrocarbon groups are bonded directly to silicon atoms in a siloxane matrix of siloxane linkage through carbon-silicon bonding.

In such polyorganosiloxanes, on average, 0.01 to 2, preferably 0.05 to 1.5, more preferably 0.1 to 1 sulfonic acid group-containing hydrocarbon groups are bonded to one silicon atom of siloxane structure through the carbon-silicon bonding, while, on average, 0.01 to 2, preferably 0.05 to 1.5, more preferably 0.1 to 1 mercapto group-containing hydrocarbon groups are bonded to one silicon atom. The total of hydrocarbon groups containing sulfonic acid groups bonded to silicon atoms and those containing mercapto groups bonded to silicon atoms is, on average, 0.05 to 3, preferably 0.1 to 2, and more preferably 0.2 to 1 relative to one silicon atom.

The polyorganosiloxane having both a sulfonic acid group and a mercapto group-containing hydrocarbon group used as a catalyst in the present invention may be prepared by any method, as long as sulfonic acid group-containing and mercapto group-containing hydrocarbon groups directly bonded to silicon atoms through the carbon-silicon bonding exist in a polysiloxane (silica) matrix. The polyorganosiloxane may be prepared according to one of the following methods, however, the invention is not restricted by the methods of preparation below.

One preferable method is hydrolyzing a mixture of at least one silane compound expressed by the general formula of $X_nSi(R_3)_{4-n}$, wherein n is an integer of from 1 to 3; X is at least one selected from the group consisting of a chlorine atom, a bromine atom, an iodine atom, and an alkoxyl group; $R_3$ is at least one selected from hydrocarbon groups having at least one sulfonic acid group; and Si represents a silicon atom, and a silane compound expressed by the general formula of $X_nSi(R_2)_{4-n}$, wherein n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom.

Another possible method is hydrolyzing a mixture of silane compounds described above and at least one silane compound expressed by the general formula of $SiX_4$, wherein X is at least one selected from the group consisting of a chlorine atom, a bromine atom, an iodine atom, and an alkoxyl group; and Si represents a silicon atom.

Still another possible method includes the following steps of:

hydrolyzing at least one silane compound expressed by the general formula of $X_nSi(R_3)_{4-n}$, wherein n is an integer of from 1 to 3; X is at least one selected from the group consisting of a chlorine atom, a bromine atom, an iodine atom, and an alkoxyl group; $R_3$ is at least one selected from hydrocarbon groups having at least one sulfonic acid group; and Si represents a silicon atom, or a mixture of the above silane and at least one silane compound expressed by the general formula of $SiX_4$ to yield a polyorganosiloxane having a sulfonic acid group, wherein X is at least one selected from the group consisting of a chlorine atom, a bromine atom, an iodine atom, and an alkoxyl group; and Si represents a silicon atom;

silylating the sulfonic acid group-containing polyorganosiloxane with a silane compound expressed by the general formula of $X_nSi(R_2)_{4-n}$, wherein n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom; and hydrolyzing the silylated compound to yield a polyorganosiloxane having both a mercapto group-containing hydrocarbon group and a sulfonic acid group.

According to one preferable application of this process, the hydrolyzation is carried out after protons of sulfonic acid groups are replaced with metal cations, and then the resulting polyorganosiloxane is treated with an acid to replace the metal cations with protons.

Successive or simultaneous silylation of the silane compounds expressed by the general formulae of $X_nSi(R_3)_{4-n}$ and $X_nSi(R_2)_{4-n}$ gives a polyorganosiloxane fixed sulfonic acid groups and mercapto groups, which is also applicable as a catalyst to the present invention.

Another preferable method of preparation includes the following steps:

hydrolyzing at least one silane compound expressed by the general formula of $X_nSi(R_1)_{4-n}$, wherein n is an integer of from 1 to 3; X is at least one selected from the group consisting of a chlorine atom, a bromine atom, an iodine atom, and an alkoxyl group; $R_1$ is at least one hydrocarbon group selected from the group consisting of 1 to 20 carbon atoms-containing hydrocarbon groups having at least one mercapto group (—SH), 6 to 20 carbon atoms-containing hydrocarbon groups having an aromatic group, 1 to 15 carbon atoms-containing alkyl groups having at least one halogen atom, 2 to 15 carbon atoms-containing olefinic hydrocarbon groups having at least one carbon-carbon unsaturated double bond, and 2 to 15 carbon atoms-containing hydrocarbon groups having at least one epoxy group; and Si represents a silicon atom;

or a mixture of the above silane and at least one silane compound expressed by the general formula of $SiX_4$ to yield a polyorganosiloxane, wherein X is at least one selected from the group consisting of a chlorine atom, a bromine atom, an iodine atom, and an alkoxyl group; and Si represents a silicon atom;

sulfonating the hydrocarbon group $R_1$ contained in the above polyorganosiloxane to yield a polyorganosiloxane having a sulfonic acid group;

silylating the sulfonic acid group-containing polyorganosiloxane with at least one silane compound expressed by the general formula of $X_nSi(R_2)_{4-n}$, wherein n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom; and hydrolyzing the silylated polyorganosiloxane to yield a polyorganosiloxane having both a mercapto group-containing hydrocarbon group and a sulfonic acid group.

Still another preferable method of preparing a polyorganosiloxane having both a sulfonic acid group and a mercapto group-containing hydrocarbon group includes the following steps of:

silylating silica gel with at least one silane compound expressed by the general formula of $X_nSi(R_1)_{4-n}$ and hydrolyzing the silylated compound to yield a polyorganosiloxane, wherein n is an integer of from 1 to 3; X is at least one selected from the group consisting of a chlorine atom, a bromine atom, an iodine atom, and an alkoxyl group; $R_1$ is at least one hydrocarbon group selected from the group consisting of 1 to 20 carbon atoms-containing hydrocarbon groups having at least one mercapto group (—SH), 6 to 20 carbon atoms-containing hydrocarbon groups having an aromatic group, 1 to 15 carbon atoms-containing alkyl groups having at least one halogen atom, 2 to 15 carbon atoms-containing olefinic hydrocarbon groups having at least one carbon-carbon unsaturated double bond, and 2 to 15 carbon atoms-containing hydrocarbon groups having at least one epoxy group; and Si represents a silicon atom;

sulfonating the polyorganosiloxane to yield a polyorganosiloxane having a sulfonic acid group;

silylating the sulfonic acid group-containing polyorganosiloxane with at least one silane compound expressed by the general formula of $X_nSi(R_2)_{4-n}$, wherein n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom; and hydrolyzing the silylated polyorganosiloxane.

The hydrocarbon groups $R_1$, $R_2$, and $R_3$ included in the above general formulae are described more in detail.

$R_3$ may be any hydrocarbon group having at least one sulfonic acid group (—SO$_3$H), and is preferably a hydrocarbon group containing carbon atoms of from 1 to 20 having at least one sulfonic acid group. More concretely $R_3$ is at least one hydrocarbon group selected from the group consisting of substituted or non-substituted aromatic hydrocarbon groups preferably containing 6 to 20 carbon atoms, more preferably containing 6 to 15 carbon atoms and having at least one sulfonic acid group, and substituted or non-substituted aliphatic and alicyclic hydrocarbon groups preferably containing 1 to 15 carbon atoms, more preferably containing 1 to 10 carbon atoms and having at least one sulfonic acid group. In the aromatic hydrocarbon groups, a sulfonic acid group may substitute an aromatic group directly or via an aromatic group-substituted hydrocarbon group.

Possible examples include: aromatic groups such as phenyl group, tolyl group, naphthyl group, and methylnaphthyl group in which at least one sulfonic acid group is substituted on the aromatic rings; aromatic-substituted alkyl groups such as benzyl group and naphthylmethyl group in which at least one sulfonic acid group is substituted on the aromatic rings; and methyl group, ethyl group, n-propyl group, i-propyl group, n-butyl group, i-butyl group, t-butyl group, straight or branched pentyl groups, straight or branched hexyl groups, straight or branched heptyl group and straight or branched octyl groups, cyclohexyl group, methylcyclohexyl group, and ethylcyclohexyl group all of which are substituted by at least one sulfonic acid group. These aromatic hydrocarbon groups, or aliphatic or alicyclic saturated hydrocarbon groups may have substituent groups like halogen atoms, alkoxyl groups, nitro groups, amino groups, and hydroxyl groups, in addition to the sulfonic acid group.

$R_2$ is at least one selected from 1 to 20 carbon atoms-containing hydrocarbon groups having at least one mercapto group expressed by the rational formula of —SH, wherein —SH group is bonded to an aliphatic or alicyclic saturated hydrocarbon, an unsaturated hydrocarbon, or an aromatic hydrocarbon. Preferably $R_2$ is a hydrocarbon group having at least one —SH group bonded to an aliphatic or alicyclic saturated hydrocarbon group or an aromatic hydrocarbon group. Concrete examples include: mercaptoalkyl groups such as mercaptomethyl group, 2-mercaptoethyl group, and 3-mercapto-n-propyl group; alicyclic hydrocarbon groups such as 4-mercaptocyclohexyl group and 4-mercaptomethylcyclohexyl group; and mercaptoaromatic groups, such as 4-mercaptophenyl group and 4-mercaptomethylphenyl group, however, the present invention is not limited to these examples. These aromatic hydrocarbon groups, or aliphatic or alicyclic saturated hydrocarbon groups may have substituent groups like halogen atoms, alkoxyl groups, nitro groups, amino groups, and hydroxyl groups, in addition to the mercapto group.

$R_1$ may be any hydrocarbon group, in which a sulfonic acid group can be introduced through one of known sulfonation processes. Preferably $R_1$ is at least one hydrocarbon group selected from the group consisting of hydrocarbon groups having at least one mercapto group (—SH), hydrocarbon groups having an aromatic group, alkyl groups having at least one halogen atom, olefinic hydrocarbon groups having at least one carbon-carbon unsaturated double bond, and hydrocarbon groups having at least one epoxy group.

The hydrocarbon group having at least one mercapto group (—SH) applicable to $R_1$ includes 1 to 20 carbon atoms-containing hydrocarbon groups, wherein an —SH group is bonded to an aliphatic or alicyclic saturated hydrocarbon, an unsaturated hydrocarbon, or an aromatic hydrocarbon. It is preferable that the hydrocarbon group has at least one —SH group bonded to an aliphatic or alicyclic saturated hydrocarbon group or an aromatic hydrocarbon group. Concrete examples include: mercaptoalkyl groups such as mercaptomethyl group, 2-mercaptoethyl group, and 3-mercapto-n-propyl group; alicyclic hydrocarbon groups such as 4-mercaptocyclohexyl group and 4-mercaptomethylcyclohexyl group; and mercaptoaromatic groups such as 4-mercaptophenyl group and 4-mercaptomethylphenyl group, however, the present invention is not limited to these examples. These aromatic hydrocarbon groups, or aliphatic or alicyclic saturated hydrocarbon groups may have substituent groups like halogen atoms, alkoxyl groups, nitro groups, amino groups, and hydroxyl groups, in addition to the mercapto group.

Aromatic group-containing hydrocarbon groups and aromatic-substituted hydrocarbon groups (for example, alkyl groups substituted by aromatic groups) containing carbon atoms of from 6 to 20, preferably from 6 to 15 are applicable for the hydrocarbon group having an aromatic group. Concrete examples include aromatic groups such as phenyl group, tolyl group, xylyl group, methylnaphthyl group, and ethylnaphthyl group, and aromatic-substituted alkyl groups such as benzyl group and naphthylmethyl group. These hydrocarbon groups may have other substituent groups like halogen atoms, alkoxyl groups, nitro groups, amino groups, and hydroxyl groups.

Halogen atom-substituted alkyl groups containing carbon atoms of from 1 to 15, preferably 1 to 10 are applicable for the alkyl group having at least one halogen atom, where the substituent halogen atom is at least one selected from the group consisting of chlorine atom, bromine atom, and iodine atom. Concrete examples include: alkyl halide groups such as chloromethyl group, dichloromethyl group, bromomethyl group, dibromomethyl group, iodomethyl group, diiodomethyl group, 2-chloroethyl group, 1,2-dichloroethyl group, 2-bromoethyl group, 2-iodoethyl group, 3-chloro-n-propyl group, 3-bromo-n-propyl group, 3-iodo-n-propyl group, 4-chloro-n-butyl group, and 4-bromo-n-butyl group; and aliphatic hydrocarbon halide groups such as 4-chlorocyclohexyl group and 4-bromocyclohexyl group.

These alkyl groups may have other substituent groups like alkoxyl groups, nitro groups, amino groups, and hydroxyl groups, in addition to the halogen atom.

Olefinic hydrocarbon groups containing carbon atoms of from 2 to 15 are applicable for the olefinic hydrocarbon group having at least one carbon-carbon unsaturated double bond. Preferably applicable are 8 to 15 carbon atoms-containing aromatic hydrocarbon groups having an olefinic hydrocarbon group as a substituent or 2 to 10 carbon atoms-containing aliphatic or alicyclic olefinic hydrocarbon groups. Concrete examples of the aromatic hydrocarbon group having an olefinic hydrocarbon group as a substituent include 4-vinylphenyl group, 4-vinylnaphthyl group, and 4-allylphenyl group, and those of the aliphatic and alicyclic olefinic hydrocarbon group include vinyl group, allyl group, n-butenyl groups, cyclohexenyl groups, methylcyclohexenyl groups, and ethylcyclohexenyl groups. These hydrocarbon groups may have other substituent groups like halogen atoms, alkoxyl groups, nitro groups, amino groups, and hydroxyl groups.

Hydrocarbon groups containing carbon atoms of from 2 to 15 having at least one epoxy group are applicable for the hydrocarbon group having at least one epoxy group. Preferably applicable are 8 to 15 carbon atoms-containing aromatic hydrocarbon groups having an epoxy group as a substituent or 2 to 10 carbon atoms-containing aliphatic or alicyclic hydrocarbon groups having epoxy bonding. Concrete examples of the aromatic hydrocarbon group having an epoxy group as a substituent include p-epoxyethylphenyl group, 4-epoxyethylnaphthyl group, 4-(2,3-epoxypropyl)phenyl group, and 4-(3,4-epoxycyclohexyl)phenyl group, and those of the aliphatic or alicyclic hydrocarbon group having epoxy linkage include epoxyethyl group, 2,3-epoxypropyl group, 3,4-epoxycyclohexyl group, 3-glycidoxypropyl group, and 2-(3,4-epoxycyclohexyl)ethyl group. These hydrocarbon groups may have other substituent groups like halogen atoms, alkoxyl groups, nitro groups, amino groups, and hydroxyl groups, in addition to the epoxy group.

These hydrocarbon groups applied for $R_1$ are only examples and not restrictive in any sense, since $R_1$ may be any hydrocarbon group, in which a sulfonic acid group can be introduced through one of known sulfonation processes.

As described previously, the polyorganosiloxane having both a sulfonic acid group and a mercapto group-containing hydrocarbon group is prepared by the following steps of:

hydrolyzing a silane compound expressed by the general formula of $X_nSi(R_1)_{4-n}$ or a mixture of that silane compound and another silane compound expressed by the general formula of $SiX_4$, or alternatively silylating a silane compound expressed by the general formula of $X_nSi(R_1)_{4-n}$ on silica gel and hydrolyzing the silylated compound to yield a polyorganosiloxane;

sulfonating the polyorganosiloxane to yield a polyorganosiloxane having a sulfonic acid group;

silylating the sulfonic acid group-containing polyorganosiloxane with a silane compound expressed by the general formula of $X_nSi(R_2)_{4-n}$; and hydrolyzing the silylated polyorganosiloxane.

Any sulfonation process may be applied in the method of the present invention, as long as the hydrocarbon group $R_1$ can be sulfonated to the sulfonic acid group-containing hydrocarbon group. Different hydrocarbon groups applied for $R_1$ naturally have different sulfonation processes.

As for a polyorganosiloxane obtained from a silane compound having at least one mercapto group-containing hydrocarbon group, a polyorganosiloxane having a sulfonic acid group is prepared by bringing the polyorganosiloxane into contact with an oxidizing agent, such as nitric acid or hydrogen peroxide, for oxidation or by the addition reaction of a sulfonic acid group-containing olefin compound (addition of —SH group to olefin). In the latter process, adding a smaller quantity of the sulfonic acid group-containing olefin compound than that of mercapto group in the mercapto group-containing polyorganosiloxane allows the polyorganosiloxane having both a sulfonic acid group and a mercapto group to be yielded without the subsequent silylating process with a silane compound expressed by the general formula of $X_nSi(R_2)_{4-n}$.

Typical examples of the sulfonic acid group-containing olefin compound used for the sulfonation process include vinyl sulfonic acid, allyl sulfonic acid, methallyl sulfonic acid, styrene sulfonic acid, and cyclohexene sulfonic acid, however, the present invention is not limited to these olefin sulfonic acids.

For a polyorganosiloxane to be obtained from a silane compound having an aromatic group-containing hydrocarbon group, the sulfonic acid group-containing polyorganosiloxane is prepared by a standard sulfonating process for aromatic compounds, that is, bringing the polyorganosiloxane into contact with sulfuric acid or chlorosulfonic acid.

As for a polyorganosiloxane obtained from a silane compound having an alkyl halide group, the sulfonic acid group-containing polyorganosiloxane is prepared through contact of the polyorganosiloxane with a solution of metal sulfite such as sodium sulfite and potassium sulfite, under the heating condition and the subsequent acid treatment.

In the case of a polyorganosiloxane obtained from a silane compound having an olefinichydrocarbon group having at least one carbon-carbon unsaturated double bond, the sulfonic acid group-containing polyorganosiloxane is prepared through contact of the polyorganosiloxane with a solution of metal hydrogensulfite such as sodium hydrogensulfite and potassium hydrogensulfite, in the presence of an oxidizing agent like the air or oxygen and the subsequent acid treatment.

For a polyorganosiloxane obtained from a silane compound having at least one epoxy group (oxirane group), the sulfonic acid group-containing polyorganosiloxane is prepared through contact of the polyorganosiloxane with a solution of metal hydrogensulfite such as sodium hydrogensulfite and potassium hydrogensulfite, and the subsequent acid treatment.

It is preferable that a metal sulfate coexists in the sulfonation process using a metal hydrogensulfite. The present invention is not restricted to these sulfonation processes.

In the process for the present invention, the polyorganosiloxane having both a sulfonic acid group and a mercapto group-containing hydrocarbon group is obtained by silylating the sulfonic acid group-containing polyorganosiloxane thus prepared with a silane compound expressed by the general formula of $X_nSi(R_2)_{4-n}$, and hydrolyzing the silylated polyorganosiloxane.

The silylation process applied in the present invention is realized with any of the known silylating agents.

One typical method makes a silanol group (—Si—OH) included in the sulfonic acid group-containing polyorganosiloxane matrix obtained by the above process directly react with the silane compound expressed by the general formula of $X_nSi(R_2)_{4-n}$ to give a siloxane linkage (Si—O—Si—$R_2$) for fixation on the polysiloxane (including silica gel). Contact of the sulfonic acid group-containing polyorganosiloxane with a large quantity of silylating agent in the presence of water results in fixing a large quantity of mercapto group-containing hydrocarbon groups.

According to a preferable application, protons of sulfonic acid groups in the sulfonic acid group-containing polyorganosiloxane are substituted by metal cations prior to the silylation process, and the metal cations are reconverted to protons with an acid after the silylation.

In the silylation process, the silylating agent may be diluted with a medium inactive to the silylating agent and the sulfonic acid group-containing polyorganosiloxane. Examples of such a medium include alcohols, aliphatic saturated hydrocarbons such as hexane and heptane, and aromatic hydrocarbons such as benzene and toluene.

The quantity of silylation with the silylating agent (that is, an increase in weight after silylation and hydrolysis) is not restricted in the present invention, but is preferably 0.5 to 200, more specifically 1 to 100 percent by weight relative to the starting material, the sulfonic acid group-containing polyorganosiloxane.

In the above general formulae, X is at least one selected from the group consisting of a chlorine atom, a bromine atom, an iodine atom, and an alkoxyl group and works to allow decomposition of the silicon-X linkage by hydrolysis to give a polysiloxane linkage. Concrete examples of the alkoxyl group include alkylalkoxyl groups such as methoxyl group, ethoxyl group, n-propoxyl group, isopropoxyl group, n-butoxyl group, sec-butoxyl group, and t-butoxyl group, and aromatic alkoxyl groups like phenoxyl group and naphthoxyl group, however, the present invention is not restricted to these examples. Chlorine atom is also an preferable alternative for X. X is not restricted to the above examples, and may be, for example, a mixture of some of these substituent groups.

Conditions described below are preferably applied for the process for the present invention.

The mixing ratio of phenol to acetone used as raw materials is not restricted, but the molar ratio of phenol to acetone is preferably 0.1 to 100, more preferably 0.5 through 50. The excessively small amount of phenol results in the relatively low conversion of acetone, while the excessively large amount of phenol, which attains the high conversion of acetone, requires a bulky reaction vessel and massive circulation of phenol, thereby lowering the efficiency of production.

The reaction temperature is not specifically restricted in the invention, but is preferably 0° C. to 300° C., more preferably 30° C. through 300° C. An extremely low reaction temperature requires a very long time to attain the high conversion of raw materials. This means extremely low reaction rate and results in lowering the productivity of the reaction product. An extremely high reaction temperature, on the other hand, allows an undesirable side reaction to increase formation of by-products. This adversely affects the stability of raw materials, phenol and acetone, as well as the reaction product, bisphenol A, and lowers the reaction selectivity resulting in poor cost performance.

The reaction may proceed under applied pressure, under reduced pressure, or at atmospheric pressure. An excessively low pressure is not desirable to attain the sufficient reaction efficiency per unit volume. The preferable pressure range for the reaction is between 0.1 and 200 arm, more preferably between 0.5 and 100 atm, however, the present invention is not restricted to such pressure range.

The quantities of acid catalyst and cocatalyst, that is, a polyorganosiloxane having a mercapto group-containing hydrocarbon group, used in the present invention are not specifically restricted. In batch reaction, the preferable quantity for both the acid catalyst and the cocatalyst is 0.001 to 200 percent by weight, more preferably 0.1 to 50 percent by weight relative to phenol used as a starting material.

The quantity of a polyorganosiloxane having both a sulfonic acid group and a mercapto group-containing hydrocarbon group used as a catalyst is not restricted in the present invention, but is preferably 0.002 to 200 percent by weight, more preferably 0.1 to 50 percent by weight relative to phenol used as a starting material.

An extremely small amount of the acid catalyst and the polyorganosiloxane having a mercapto group-containing hydrocarbon group used as the cocatalyst or that of polyorganosiloxane having both a sulfonic acid group and a mercapto group-containing hydrocarbon group used as the catalyst remarkably lowers the reaction rate and reaction efficiency. An extremely large amount, on the other hand, lowers the stirring efficiency of reaction solutions, which may result in some troubles and problems in batch reaction.

A solvent or gas inert to substances concerned in the reaction as well as the acid catalyst and the polyorganosiloxane having a mercapto group-containing hydrocarbon group used as the cocatalyst or the polyorganosiloxane having both a sulfonic acid group and a mercapto group-containing hydrocarbon group used as the catalyst may be added for the purpose of dilution in the reaction system. Applicable diluents include aliphatic saturated hydrocarbons like methane, ethane, propane, butane, hexane, and cyclohexane, and inert gases like nitrogen, argon, and helium, and hydrogen in some cases.

The process for the present invention may be carried out in batch, semi-batch, or flow systems.

The reaction may proceed in the liquid phase, gas phase, or gas-liquid phase, while the acid catalyst is in homogeneous liquid or heterogeneous solid, and the polyorganosiloxane having a mercapto group-containing hydrocarbon group is in solid form or the polyorganosiloxane having both a sulfonic acid group and a mercapto group-containing hydrocarbon group is in solid form. The liquid phase reaction is preferable for the better reaction efficiency.

The polyorganosiloxane having a mercapto group-containing hydrocarbon group used as the cocatalyst or the polyorganosiloxane having both a sulfonic acid group and a mercapto group-containing hydrocarbon group used as the catalyst may be charged in any type of reactor, for example, fixed bed, fluidized bed, suspended bed, or plate fixed bed.

The reaction time (residence time or catalytic contact time in the flow system) is not specifically restricted, but is generally 0.1 second to 30 hours, more preferably 0.5 second to 15 hours.

After the completion of the reaction, the reaction product is separated from the cocatalyst, acid catalyst, and other additives through filtration, extraction, or distillation.

The final product or bisphenol A is separated from the reaction mixture and purified by any of known separation and purification processes such as solvent extraction, distillation, or treatment with alkali or acid, or combination of these processes. In a preferable application, non-reacted raw materials are recovered and recycled into the reaction system.

In the batch reaction, after separation of the reaction product, the acid catalyst and cocatalyst or the catalyst with fixed cocatalyst can be recycled to the reaction system with or without partial or whole regeneration.

In the fixed bed or fluidized bed flow system, when part or all of the acid catalyst or cocatalyst deactivates or lowers its activity, the acid catalyst and/or cocatalyst or the catalyst with fixed cocatalyst can be regenerated after interruption of the reaction and returned to the reaction system. Alternatively, part of such catalysts can be taken out of the system continuously or intermittently and recycled to the reaction vessel after regeneration. New acid catalyst and cocatalyst or catalyst with fixed cocatalyst can also be supplied to the reaction vessel continuously or intermittently. In the moving bed flow system or homogeneous catalyst flow system, like the batch reaction system, the acid catalyst and/or cocatalyst or the catalyst with fixed cocatalyst can be separated from the reaction mixture and recycled to the reaction system with or without partial or whole regeneration.

EXAMPLES

Concrete examples of the present invention are given below, however, these examples are only illustrative and not restrictive in any sense.

A. Preparation of mercapto group-containing polyorganosiloxanes used as cocatalysts (a) Cocatalyst 1

In a 500 ml three-necked flask with an agitator and a reflux condenser, 100 ml of ethanol and 10.0 g (51.7 mmol) of 3-mercaptopropyl trimethoxysilane [$(HSCH_2CH_2CH_2)Si(OMe)_3$] were stirred at room temperature for two hours. Five times ($51.7 \times 3 \times 0.5 \times 5 = 387.8$ mmol) as much pure water as the required mole amount (half of the moles of the alkoxyl group included in the silane compound) was slowly added dropwise to the reaction mixture, and the mixed solution was further stirred at room temperature for one hour. After 10.0 g of 28% aqueous ammonia was added dropwise to the solution in approximately one hour with stirring, the reaction solution was heated to 80° C. and stirred for 24 hours while heating. This made the reaction solution set to a gel. A solid substance was obtained by evaporating the solvent under reduced pressure. The solid substance was washed with 500 ml of pure water with stirring at 80° C. for four hours. After the solution was cooled, a solid substance was separated from the solution by filtration, sufficiently washed with pure water, and dried under reduced pressure at 100° C. for four hours to yield a polyorganosiloxane having a mercapto group. This was used as Cocatalyst 1 in the reaction.

(b) Cocatalysts 2 to 4

Tetraethoxysilane was added to 10.0 g of 3-mercaptopropyl trimethoxysilane by the respective amounts specified in Table 1. After the stirring process like the preparation of Cocatalyst 1, pure water of five times the required amount of pure water for hydrolysis, that is, five times a half of the total moles of the methoxyl group and the ethoxyl group, was added dropwise. The subsequent steps were executed in the same manner as the above to yield Cocatalysts 2 to 4.

(c) Cocatalyst 5

Cocatalyst 5 was prepared under the same conditions and in the same operations as the preparation of Cocatalyst 2, except that 10.0 g of 3-mercaptopropyl trimethoxysilane was replaced by 10.0 g of 3-mercaptopropyl-methyl dimethoxysilane [$(HSCH_2CH_2CH_2)Si(Me)(OMe)_2$].

The amounts of silane compounds and properties of Cocatalysts 1 to 5 are shown in Table 1.

(d) Cocatalyst 6

After 10.0 g of a commercially available silica gel (MS gel manufactured by Dokai Chemical Industries Ltd.,) was dried under reduced pressure at 100° C. for four hours, 10.0 g (51.7 mmol) of 3-mercaptopropyl trimethoxysilane [$(HSCH_2CH_2CH_2)Si(OMe)_3$] was added to the dried silica gel and stirred at 100° C. for four hours. After the solution was cooled, a solid substance was separated by filtration and sufficiently washed with methanol and acetone. A polyorganosiloxane having a mercapto group-containing hydrocarbon group contained 1.11 mgeq/g of mercapto group.

TABLE 1

| Cocatalyst | Silane compounds used for hydrolysis | | | Quantity of SH (mgeq/g) |
|---|---|---|---|---|
| | Mercaptosilanes | (g) | Silanes (g) | |
| Cocatalyst 1 | $(HSCH_2CH_2CH_2)Si(OMe)_3$ | 10.0 | Not used 0.0 | 1.77 |
| Cocatalyst 2 | $(HSCH_2CH_2CH_2)Si(OMe)_3$ | 10.0 | $Si(OEt)_4$ 10.0 | 2.71 |
| Cocatalyst 3 | $(HSCH_2CH_2CH_2)Si(OMe)_3$ | 10.0 | $Si(OEt)_4$ 5.0 | 2.99 |
| Cocatalyst 4 | $(HSCH_2CH_2CH_2)Si(OMe)_3$ | 10.0 | $Si(OEt)_4$ 20.0 | 2.49 |
| Cocatalyst 5 | $(HSCH_2CH_2CH_2)Si(Me)(OMe)_2$ | 10.0 | $Si(OEt)_4$ 10.0 | 2.55 |
| Cocatalyst 6 | | | | 1.11 |

Examples 1 to 6

In a 70 ml pressure reaction vessel, 3.80 g (65.5 mmol) of acetone, 33.00 g (351.1 mmol) of phenol, 2.00 g of an acid catalyst, and 0.60 g of each one of the Cocatalysts 1 to 6 were stirred at 100° C. for two hours after pressurized to a gauge pressure of 5 kg/cm$^2$ with nitrogen gas. The acid catalyst used here was a partially neutralized heterogeneous salt [$(NH_4)_2HPW_{12}O_{40}$], where ⅔ of the protons included in dodecatungstophosphoric acid were exchanged with ammonium cations. After the completion of the reaction, each reaction solution was cooled to the room temperature and reduced to ordinary pressure. The reaction solutions were then analyzed by liquid chromatography. Bisphenol A was produced in high yields as shown in Table 2.

Comparative Example 1

The reaction took place under the same conditions as Example 2, except that no cocatalyst was used. Both the yield of bisphenol A and 4,4'-selectivity of bisphenol A were lower as shown in Table 2.

This shows the excellent catalytic activity of the mercapto group-containing polyorganosiloxane used as the cocatalyst in the present invention.

Example 7

The reaction took place under the same conditions as Example 2, except that the acid catalyst used was 2.0 g of dodecatungstophosphoric acid dehydrated the its water of crystallization ($H_3PW_{12}O_{40} \cdot OH_2O$). Results are shown in Table 2.

Comparative Example 2

The reaction took place under the same conditions as Example 7, except that no cocatalyst was used. Both the yield and selectivity of bisphenol A were lower than those of Example 7 as shown in Table 2. This shows that the cocatalyst of the present invention is effective for the homogeneous acid catalyst.

Example 8

The reaction took place under the same conditions as Example 2, except that the acid catalyst used was 2.0 g of a heterogeneous solid catalyst ($Cs_2HPW_{12}O_{40} \cdot OH_2O$), where ⅔ of the protons included in dodecatungstophosphoric acid were exchanged with Cs cations. Results are shown in Table 2.

Example 9

The reaction took place under the same conditions as Example 2, except that the acid catalyst used was 2.0 g of a strongly acidic cation exchange resin, Amberlyst 15 (manufactured by Rohm & Haas Co.). Results are shown in Table 2.

Comparative Example 3

The reaction took place under the same conditions as Example 9, except that the cocatalyst, mercapto group-containing polyorganosiloxane, was not used. Both the yield and selectivity of bisphenol A were lower than those of Example 9 as shown in Table 2.

Example 10

The reaction took place under the same conditions as Example 2, except that the quantity of acetone used was 1.90 g. Example 10 gave high yield of bisphenol A relative to the input acetone as shown in Table 2.

Example 11

The reaction took place under the same conditions as Example 2, except that the reaction temperature was 120° C. and the reaction time was one hour. Example 11 gave a high yield of bisphenol A shown in Table 2.

Example 12

The reaction took place under the same conditions as Example 2, except that the quantity of Cocatalyst 2 added was 1.2 g. An increase in quantity of the cocatalyst enhanced the yield and the selectivity of bisphenol A as shown in Table 2.

Example 13

The reaction took place under the same conditions as Example 2, except that the acid catalyst used was 2.0 g of dodecatungstosilicic acid dehydrated of its water of crystallization ($H_4SiW_{12}O_{40} \cdot H_2O$). Results are shown in Table 2.

Comparative Example 4

The reaction took place under the same conditions as Example 13, except that the cocatalyst, mercapto group-containing polyorganosiloxane, was not used. Both the yield and selectivity of bisphenol A were lower than those of Example 13 as shown in Table 2.

Example 14

The reaction took place under the same conditions as Example 2, except that the acid catalyst used was 2.0 g of concentrated hydrochloric acid. Results are shown in Table 2.

Comparative Example 5

The reaction took place under the same conditions as Example 14, except that the cocatalyst, mercapto group-containing polyorganosiloxane, was not used. Both the yield and selectivity of bisphenol A were lower than those of Example 14 as shown in Table 2.

Example 15

The cocatalyst used in Example 14 was collected by filtering out the reaction solution, sufficiently washed with methanol, and dried. The dried cocatalyst was used again in the reaction under the same conditions as Example 14. The recycled cocatalyst maintained its activity as shown in Table 2.

TABLE 2

| | | Yield of products (% based on input acetone) | | |
|---|---|---|---|---|
| | Cocatalysts | 4,4'-BPA | 2,4'-BPA | COD |
| Example 1 | 1 | 36.7 | 2.9 | 1.2 |
| Example 2 | 2 | 47.2 | 3.0 | 1.6 |
| Example 3 | 3 | 49.4 | 3.1 | 1.3 |
| Example 4 | 4 | 46.1 | 3.5 | 0.9 |
| Example 5 | 5 | 47.0 | 2.9 | 1.0 |
| Example 6 | 6 | 43.0 | 2.1 | 0.6 |
| Comparative Example 1 | — | 27.9 | 5.1 | 2.0 |
| Example 7 | 2 | 54.4 | 2.8 | 1.1 |
| Comparative Example 2 | — | 30.2 | 5.7 | 2.4 |
| Example 8 | 2 | 30.5 | 2.1 | 0.8 |
| Example 9 | 2 | 36.8 | 2.2 | 0.9 |
| Comparative Example 3 | — | 12.4 | 1.3 | 0.7 |
| Example 10 | 2 | 87.6 | 3.0 | 3.0 |
| Example 11 | 2 | 49.2 | 3.4 | 1.7 |
| Example 12 | 2 | 55.3 | 2.8 | 1.5 |
| Example 13 | 2 | 52.5 | 2.8 | 1.0 |
| Comparative Example 4 | — | 29.0 | 5.5 | 2.5 |
| Example 14 | 2 | 52.1 | 2.0 | 1.0 |
| Comparative Example 5 | — | 22.0 | 2.3 | 1.5 |
| Example 15 | 2 | 52.4 | 2.1 | 1.0 |

4,4'-BPA: 2,2-bis(4'-hydroxyphenyl)propane,
2,4'-BPA: 2-(2'-hydroxyphenyl)-2-(4'-hydroxyphenyl)propane (isomer),
COD: 2,2,4-trimethyl-4-(4'-hydroxyphenyl)chroman (by-product of reaction)

B: Preparation of polyorganosiloxanes having both a sulfonic acid group and a mercapto group-containing hydrocarbon group used as catalysts (Table 4 shows properties of catalysts prepared as below.)

(e) Catalyst 1

After 1.57 g (7.64 mmol) of sodium styrene sulfonate, 10 ml of water, and 3 ml of concentrated hydrochloric acid were added to 2.82 g (content of mercapto group: 7.64 mmol) of Cocatalyst 2, mercapto group-containing polyorganosiloxane prepared from the same weight of 3-mercaptopropyl trimethoxysilane and tetraethoxysilane, in a 100 ml eggplant type flask, the mixture was heated and stirred under reflux for one hour. After the reaction mixture was cooled, a white solid substance was separated by filtration and was sufficiently washed with a large amount of water until the filtrate became neutral. The washed solid substance was dried at 100° C. for four hours to yield a polyorganosiloxane having a sulfonic acid group and a mercapto group-containing hydrocarbon group. This was used as Catalyst 1 in the reaction.

(f) Catalysts 2 to 4

Catalysts 2 to 4 were prepared under the same conditions and in the same operations as preparation of Catalyst 1, except that Cocatalyst 2 was replaced by other cocatalysts as shown in Table 3.

(g) Catalysts 5 to 7

Catalysts 5 to 7 were prepared under the same conditions and in the same operations as preparation of Catalyst 1, except that the sodium styrene sulfonate was replaced by 9.62 mmol of sodium vinyl sulfonate, sodium allyl sulfonate, or sodium methallyl sulfonate as shown in Table 3.

Preparation conditions of Catalysts 1 to 7 are shown in Table 3.

(h) Catalyst 8

29 ml of 0.01N hydrochloric acid was added dropwise to a mixture of 0.60 mol of $Cl(CH_2)_3Si(OMe)_3$, 1.40 mol of $Si(OEt)_4$, and 200 ml of ethanol in a 1000 ml three-necked flask with an agitator and a reflux condenser. The solution was heated to 80°–90° C. and slowly concentrated through evaporation of ethanol. The resulting solution with extremely high viscosity was mixed with 180 ml of hexane and 120 ml of ethanol, and a mixture of 100 ml of 28% aqueous ammonia and 540 ml of water was then added dropwise to the solution mixture and stirred at the room temperature for four hours. A solid substance separated by filtration was washed with a large amount of water and dried at 120° C. A mixture including 15.0 g of the polyorganosiloxane thus obtained, where chloropropyl groups were fixed to the siloxane matrix, 10.32 g of $Na_2SO_3$, and 60 ml of water was stirred at 100° C. for 50 hours. After the reaction mixture was cooled, a solid substance separated by filtration was washed with a large quantity of water and treated with diluted hydrochloric acid for ion exchange from $Na^+$ to $H^+$ to yield a solid acid, where sulfonic acid groups were fixed to the siloxane matrix. After 6.0 g of the solid acid (acid content 1.25 mgeq/g) was treated with an aqueous solution of sodium chloride for ion exchange to $Na^+$ and dried under reduced pressure at 120° C. for four hours, 10 g of a mercapto group-containing silane compound $HS(CH_2)_3Si(OMe)_3$ was added to the dried solid acid and stirred at 100° C. for four hours for silylation. A solid substance separated by filtration was sufficiently washed with methanol and then with acetone for removal of non-reacted $HS(CH_2)_3Si(OMe)_3$, and treated with 6N hydrochloric acid for ion exchange to $H^+$. The product was further washed with a large quantity of pure water for the removal of the residual hydrochloric acid and dried in an oven at 120° C. for half a day to yield Catalyst 8.

(i) Catalyst 9

10.0 g of Cocatalyst 2, mercapto group-containing polyorganosiloxane prepared from same weight of 3-mercaptopropyl trimethoxysilane and tetraethoxysilane, was added gradually to 20 ml of concentrated nitric acid with stirring, and then the mixture was stirred for one hour. After the completion of the reaction, a white solid substance separated by filtration was washed with a large quantity of water and dried to yield a solid acid, where sulfonic acid groups were fixed to the siloxane matrix. After 6.0 g of the solid acid (acid content 1.70 mgeq/g) was treated with an aqueous solution of sodium chloride for ion exchange to $Na^+$ and dried under reduced pressure at 120° C. for four hours, 10 g of a mercapto group-containing silane compound $HS(CH_2)_3Si(OMe)_3$ was added to the dried solid acid and stirred at 100° C. for four hours for silylation. A solid substance separated by filtration was sufficiently washed with methanol and then with acetone for removal of non-reacted $HS(CH_2)_3Si(OMe)_3$, and treated with 6N hydrochloric acid for ion exchange to $H^+$. The product was further washed with a large quantity of pure water for removal of the residual hydrochloric acid and dried in an oven at 120° C. for half a day to yield Catalyst 9.

(j) Catalyst 10

Catalyst 10 was prepared under the same conditions and in the same operations as preparation of Catalyst 8, except that the mercapto group-containing silane compound $HS(CH_2)_3Si(OMe)_3$ used for silylation in preparation of Catalyst 8 was replaced by $HSCH_2Si(CH_3)_2(OEt)$.

(k) Catalyst 11

Catalyst 11 was prepared under the same conditions and in the same operations as preparation of Catalyst 9, except that the mercapto group-containing silane compound $HS(CH_2)_3Si(OMe)_3$ used for silylation in preparation of Catalyst 9 was replaced by $HSCH_2Si(CH_3)_2(OEt)$.

(l) Catalyst 12

In a 1000 ml three-necked flask, 49.28 g (200 mmol) of 3-glycidoxypropyl trimethoxysilane and 41.66 g (200 mmol) of triethoxysilane were mixed with 400 ml of ethanol and stirred well. After 60 g of water was slowly added dropwise to the solution mixture and an aqueous solution prepared by dissolving 7 g of $Na_2SO_3$ in 50 ml of water and 200 ml of water was further added dropwise, the reaction solution was stirred at 80° C. for 24 hours. The solvent was then evaporated, and a solid substance was dried at 120° C. for 24 hours. The dried solid substance was sufficiently washed with water and dried again to yield a polyorganosiloxane, where epoxy groups were fixed to the siloxane matrix. In a 1000 ml two-necked flask, 10 g of the polyorganosiloxane thus obtained was mixed with an aqueous solution prepared by dissolving 10.5 g of $NaHSO_3$ and 25 g of $Na_2SO_3$ in 250 ml of water and stirred at 120° C. for 6.5 hours. After the reaction mixture was cooled, a white solid substance separated by filtration was sufficiently washed with water, mixed with 200 ml of 1N hydrochloric acid in a 500 ml beaker, and stirred at the room temperature for one hour. A solid substance separated by filtration and re-treated with hydrochloric acid as above was sufficiently washed with water and dried at 110° C. After 6.0 g of a sulfonated solid acid thus obtained (acid content 0.735 mgeq/g) was treated with an aqueous solution of sodium chloride for ion exchange to $Na^+$ and then dried under reduced pressure at 120° C. for four hours, 10 g of a mercapto group-containing silane compound $HS(CH_2)_3Si(OMe)_3$ was added to the dried solid acid and stirred at 100° C. for four hours for silylation. A solid substance separated by filtration was sufficiently washed with methanol and then with acetone for removal of non-reacted $HS(CH_2)_3Si(OMe)_3$, and treated with 6N hydrochloric acid for ion exchange to $H^+$. The product was further washed with a large quantity of pure water for removal of the residual hydrochloric acid and dried in an oven at 120° C. for half a day to yield Catalyst 12.

(m) Catalyst 13

In a 1000 ml three-necked flask, 38.06 g (200 mmol) of vinyltriethoxysilane and 41.66 g (200 mmol) of triethoxysilane were mixed with 100 ml of ethanol and stirred at the room temperature for two hours. Five times (3.5 mol) as much pure water as the required mole amount (half of the moles of the alkoxyl group included in the silane compound) was then slowly added dropwise to the reaction mixture, and the mixed solution was further stirred at the room temperature for one hour. After 40.0 g of 28% aqueous ammonia was added dropwise in approximately one hour with stirring, the reaction mixture was heated to 80° C. and stirred for 24 hours while heating. This made the reaction mixture set to gel. A solid substance was obtained by evaporating the solvent under reduced pressure. The solid substance was washed with 1000 ml of pure water with stirring at 80° C. for four hours. After the solution was cooled, a solid substance was separated from the solution by filtration, sufficiently washed with pure water, and dried under reduced pressure at 100° C. for four hours to yield a polyorganosiloxane having a vinyl group. In a 1000 ml two-necked flask, 15 g of the polyorganosiloxane thus obtained was mixed with an aqueous solution prepared by dissolving 21 g of $NaHSO_3$ and 50 g of $Na_2SO_3$ in 500 ml of water and heated to 70° C. with stirring. After stirring while heating and blowing air for 46 hours, a white solid substance separated by filtration was sufficiently washed with water, mixed with 200 ml of 1N hydrochloric acid in a 500 ml beaker, and stirred at the room temperature for one hour. A solid substance separated by filtration and retreated with hydrochloric acid as above was sufficiently washed with water and dried at 110° C. for 8 hours to yield a polyorganosiloxane, where sulfonic acid groups were fixed to the siloxane matrix. After 6.0 g of the solid acid thus obtained (acid content 1.39 mgeq/g) was treated with an aqueous solution of sodium chloride for ion exchange to $Na^+$ and dried under reduced pressure at 120° C. for four hours, 10 g of $HS(CH_2)_3Si(OMe)_3$ was added to the dried solid acid and stirred at 100° C. for four hours for silylation. A solid substance separated by filtration was sufficiently washed with methanol and then with acetone for removal of non-reacted $HS(CH_2)_3Si(OMe)_3$, and treated with 6N hydrochloric acid for ion exchange to $H^+$. The product was further washed with a large quantity of pure water for removal of the residual hydrochloric acid and dried in an oven at 120° C. for half a day to yield Catalyst 13.

(n) Catalyst 14

After 10.0 g of a commercially available silica gel (MS gel manufactured by Dokai Chemical Industries Ltd.,) was dried under reduced pressure at 100° C. for four hours, 25 g of vinyltriethoxysilane was added to the dried silica gel in a 100 ml eggplant type flask and stirred at 100° C. for four hours. After the mixture was cooled, a white solid substance separated by filtration was sufficiently washed with methanol and dried at 120° C. In a 1000 ml two-necked flask, 15 g of the polyorganosiloxane thus obtained was mixed with an aqueous solution prepared by dissolving 21 g of $NaHSO_3$ and 50 g of $Na_2SO_3$ in 500 ml of water and heated to 70° C. with stirring. After stirring while heating and blowing air for 46 hours, a white solid substance separated by filtration was sufficiently washed with water, mixed with 200 ml of 1N hydrochloric acid in a 500 ml beaker, and stirred at the room temperature for one hour. A solid substance separated by filtration and re-treated with hydrochloric acid as above was sufficiently washed with water and dried at 110° C. for 8 hours to yield a polyorganosiloxane, where sulfonic acid groups were fixed to the siloxane matrix. After 6.0 g of the solid acid thus obtained (acid content 0.58 mgeq/g) was treated with an aqueous solution of sodium chloride for ion exchange to $Na^+$ and dried under reduced pressure at 120° C. for four hours, 10 g of $HS(CH_2)_3Si(OMe)_3$ was added to the dried solid acid and stirred at 100° C. for four hours for silylation. A solid substance separated by filtration was sufficiently washed with methanol and then with acetone for removal of non-reacted $HS(CH_2)_3Si(OMe)_3$, and treated with 6N hydrochloric acid for ion exchange to $H^+$. The product was further washed with a large quantity of pure water for removal of the residual hydrochloric acid and dried in an oven at 120° C. for half a day to yield Catalyst 14.

(o) Catalyst 15

After 10.0 g of a commercially available silica gel (MS gel manufactured by Dokai Chemical Industries Ltd.,) was dried under reduced pressure at 100° C. for four hours, 25 g of $Cl(CH_2)_3Si(OMe)_3$ was added to the dried silica gel in a 100 ml eggplant type flask and stirred at 100° C. for four hours for silylation. After the reaction solution was cooled, a white solid substance separated by filtration was sufficiently washed with methanol and dried at 120° C. A mixture including 15 g of the polyorganosiloxane thus obtained, 10.32 g of $Na_2SO_3$, and 60 ml of water was stirred at 100° C. for 50 hours. After the reaction solution was cooled, a solid substance separated by filtration was washed with a large quantity of water and treated with diluted hydrochloric acid for ion exchange from $Na^+$ to $H^+$ to yield a solid acid, where sulfonic acid groups were fixed to the siloxane matrix. After 6.0 g of the solid acid thus obtained (acid content 0.79 mgeq/g) was treated with an aqueous solution of sodium chloride for ion exchange to $Na^+$ and dried under reduced pressure at 120° C. for four hours, 10 g of $HS(CH_2)_3Si(OMe)_3$ was added to the dried solid acid and stirred at 100° C. for four hours for silylation. A solid substance separated by filtration was sufficiently washed with methanol and then with acetone for removal of non-reacted $HS(CH_2)_3Si(OMe)_3$, and treated with 6N hydrochloric acid for ion exchange to $H^+$. The product was further washed with a large quantity of pure water for removal of the residual hydrochloric acid and dried in an oven at 120° C. for half a day to yield Catalyst 15.

(p) Catalyst 16

After 10.0 g of a commercially available silica gel (MS gel manufactured by Dokai Chemical Industries Ltd.,) was dried under reduced pressure at 100° C. for four hours, 25 of $HS(CH_2)_3Si(OMe)_3$ was added to the dried silica gel in a 100 ml eggplant type flask and stirred at 100° C. for four hours for silylation. After the reaction solution was cooled, a white solid substance separated by filtration was sufficiently washed with methanol and dried at 120° C. 15 g of the polyorganosiloxane thus obtained was added gradually to 30 ml of concentrated nitric acid and stirred at the room temperature for one hour. After the completion of the reaction, a solid substance separated by filtration was washed with a large quantity of water and dried to yield a solid acid, where sulfonic acid groups were fixed to the siloxane matrix. After 6.0 g of the solid acid thus obtained (acid content 0.55 mgeq/g) was treated with an aqueous solution of sodium chloride for ion exchange to and dried under reduced pressure at 120° C. for four hours, 10 g of $HS(CH_2)_3Si(OMe)_3$ was added to the dried solid acid and stirred at 100° C. for four hours for silylation. A solid substance separated by filtration was sufficiently washed with methanol and then with acetone for removal of non-reacted $HS(CH_2)_3Si(OMe)_3$, and treated with 6N hydrochloric acid for ion exchange to $H^+$. The product was further washed with a large quantity of pure water for removal of the residual hydrochloric acid and dried in an oven at 120° C. for half a day to yield Catalyst 16.

(q) Catalyst 17

In a 1000 ml three-necked flask with an agitator and a reflux condenser, 16.7 ml of 0.01N hydrochloric acid were added dropwise to a mixture of 36.06 g (0.15 mol) of phenyltriethoxysilane, 72.92 g (0.35 mol) of $Si(OEt)_4$, and 62.5 ml of ethanol. The solution was heated to 80°–90° C. and slowly concentrated through evaporation of ethanol. A resulting solution with extremely high viscosity was mixed with 15 ml of hexane and 22.5 ml of ethanol, and a mixture of 25.0 ml of 28% aqueous ammonia and 135.0 ml of water was then added dropwise to the solution mixture and stirred at the room temperature for four hours. A solid substance separated by filtration was washed with a large amount of water and dried at 120° C. A mixture including 10.0 g of the polyorganosiloxane thus obtained, where phenyl groups were fixed to the siloxane matrix as functional groups, and 100 ml of concentrated sulfuric acid was stirred at 80° C. for 3 hours. After the reaction mixture was cooled, a solid substance separated by filtration was washed with a large quantity of water and dried to yield a solid acid, where sulfonic acid groups were fixed to the siloxane matrix. After 6.0 g of the solid acid (acid content 0.86 mgeq/g) was treated with an aqueous solution of sodium chloride for ion exchange to $Na^+$ and dried under reduced pressure at 120° C. for four hours, 10 g of a mercapto group-containing silane compound $HS(CH_2)_3Si(OMe)_3$ was added to the dried solid acid and stirred at 100° C. for four hours for silylation. A solid substance separated by filtration was sufficiently washed with methanol and then with acetone for removal of non-reacted $HS(CH_2)_3Si(OMe)_3$, and treated with 6N hydrochloric acid for ion exchange to $H^+$. The product was further washed with a large quantity of pure water for removal of the residual hydrochloric acid and dried in an oven at 120° C. for half a day to yield Catalyst 17.

TABLE 3

| Mercapto group-containing polyorganosiloxanes | Sulfonates | Catalysts |
| --- | --- | --- |
| Cocatalyst 2 | Sodium styrene sulfonate | Catalyst 1 |
| Cocatalyst 3 | Sodium styrene sulfonate | Catalyst 2 |
| Cocatalyst 4 | Sodium styrene sulfonate | Catalyst 3 |
| Cocatalyst 5 | Sodium styrene sulfonate | Catalyst 4 |
| Cocatalyst 2 | Sodium vinyl sulfonate | Catalyst 5 |
| Cocatalyst 2 | Sodium allyl sulfonate | Catalyst 6 |
| Cocatalyst 2 | Sodium methallyl sulfonate | Catalyst 7 |

TABLE 4

| | Results of analysis | | |
| --- | --- | --- | --- |
| Catalysts | Quantities of SH (mgeq/g) | Quantities of Acid (mgeq/g) | Atomic ratio of Si/C |
| Catalyst 1 | 2.17 | 0.50 | 0.451 |
| Catalyst 2 | 2.39 | 0.54 | 0.359 |
| Catalyst 3 | 1.99 | 0.48 | 0.605 |
| Catalyst 4 | 2.04 | 0.47 | 0.430 |
| Catalyst 5 | 2.00 | 0.67 | 0.561 |
| Catalyst 6 | 1.93 | 0.76 | 0.528 |
| Catalyst 7 | 1.80 | 0.90 | 0.500 |
| Catalyst 8 | 0.46 | 1.25 | 1.009 |
| Catalyst 9 | 0.20 | 1.70 | 0.625 |
| Catalyst 10 | 0.21 | 1.25 | 1.058 |
| Catalyst 11 | 0.13 | 1.70 | 0.632 |
| Catalyst 12 | 0.15 | 0.74 | 0.094 |
| Catalyst 13 | 0.55 | 1.39 | 0.631 |
| Catalyst 14 | 0.14 | 0.58 | 9.806 |
| Catalyst 15 | 0.15 | 0.79 | 5.477 |
| Catalyst 16 | 0.14 | 0.55 | 7.566 |
| Catalyst 17 | 0.16 | 0.86 | 0.170 |

Examples 16 through 22

In a 70 ml pressure reaction vessel, 3.80 g (65.5 mmol) of acetone, 33.00 g (351.1 mmol) of phenol, and 2.00 g of one of Catalysts 1 to 7 were stirred at 100° C. for two hours after pressurized to a Gauge pressure of 5 kg/cm² with nitrogen gas. After the completion of the reaction, each reaction solution was cooled to the room temperature and reduced to ordinary pressure. The reaction solutions were then analyzed by liquid chromatography. Bisphenol A was produced in high yields as shown in Table 5.

Example 23

The reaction took place under the same conditions as Example 16, except that the quantity of acetone used was 1.90 g. Example 23 gave bisphenol A in high yield relative to the input acetone as shown in Table 5.

Example 24

The reaction took place under the same conditions as Example 16, except that the reaction temperature was 120° C. and the reaction time was one hour. Example 24 gave bisphenol A in high yield as shown in Table 5.

Example 25

The reaction took place under the same conditions as Example 16, except that the quantity of Catalyst 1 added was 4.0 g. An increase in quantity of the catalyst enhanced the yield and selectivity of bisphenol A as shown in Table 5.

TABLE 5

| | | Yield of products (% based on input acetone) | | |
| --- | --- | --- | --- | --- |
| | Catalysts | 4, 4'-BPA | 2, 4'-BPA | COD |
| Example 16 | 1 | 36.5 | 1.9 | 1.2 |
| Example 17 | 2 | 35.2 | 2.0 | 1.4 |
| Example 18 | 3 | 35.4 | 2.1 | 1.1 |
| Example 19 | 4 | 36.1 | 2.5 | 0.9 |
| Example 20 | 5 | 29.0 | 1.9 | 1.0 |
| Example 21 | 6 | 29.4 | 1.8 | 1.1 |
| Example 22 | 7 | 30.5 | 2.0 | 0.8 |
| Example 23 | 1 | 55.8 | 2.2 | 1.1 |
| Example 24 | 1 | 56.6 | 4.0 | 3.0 |
| Example 25 | 1 | 50.2 | 2.2 | 1.5 |

4,4'-BPA: 2,2-bis(4'-hydroxyphenyl)propane,
2,4'-BPA: 2-(2'-hydroxyphenyl)-2-(4'-hydroxyphenyl)propane (isomer),
COD: 2,2,4-trimethyl-4-(4'-hydroxyphenyl)chroman (by-product of reaction)

Examples 26 to 35

In a 70 ml pressure reaction vessel, 3.80 g (65.5 mmol) of acetone, 33.00 g (351.1 mmol) of phenol, and 2.00 g of one of Catalysts 8 to 17 were stirred at 100° C. for two hours after pressurized to a gauge pressure of 5 kg/cm² with nitrogen gas. After the completion of the reaction, each reaction solution was cooled to the room temperature and reduced to ordinary pressure. The reaction solutions were then analyzed by liquid chromatography. Bisphenol A was produced in high yields as shown in Table 6.

Comparative Example 6

The reaction took place under the same conditions as Example 26, except that a sulfonic acid group-containing polyorganosiloxane without silylation was used as catalyst. Without the modified mercapto group, the yield of bisphenol A and 4,4'-selectivity of bisphenol A was lower as shown in Table 6.

Examples 36 and 37

The catalysts used in Examples 26 and 27 were collected by filtering out the reaction solution, sufficiently washed with methanol, and dried. The dried catalysts were used again in the reaction under the same conditions as Examples 26 and 27. The recycled catalysts maintained their activities as shown in Table 6.

Comparative Example 7

The reaction took place under the same conditions as Example 26, except that Catalyst 8 was replaced by a cation exchange resin, Amberlyst 15 (manufactured by Rohm & Haas Co.), where 15% of protons were exchanged with cations of cysteamine hydrochloride for modification of mercapto groups. Results are shown in Table 6.

Comparative Example 8

The catalyst used in Comparative Example 7 was collected by filtering out the reaction solution, sufficiently washed with methanol, and dried. The dried catalyst was used again in the reaction under the same conditions as Example 26. The recycled catalyst had a little lower activity and 4,4'-selectivity of bisphenol A as shown in Table 6.

Example 38

The reaction took place under the same conditions as Example 26, except that the reaction temperature was 120° C. This increased the yield of bisphenol A but lowered 4,4'-selectivity of bisphenol A as shown in Table 6.

Example 39

The reaction took place under the same conditions as Example 26, except that the quantity of acetone used was reduced to half, 1.90 g (32.8 mmol). The large phenol/acetone ratio resulted in increasing the yield of bisphenol A as shown in Table 6.

TABLE 6

| | | Yield of products (% based on input acetone) | | |
|---|---|---|---|---|
| | Catalysts | 4, 4'-BPA | 2, 4'-BPA | COD |
| Example 26 | 8 | 45.7 | 1.6 | 0.5 |
| Example 27 | 9 | 44.9 | 1.0 | 0.3 |
| Example 28 | 10 | 43.9 | 1.6 | 0.5 |
| Example 29 | 11 | 40.1 | 1.0 | 0.5 |
| Example 30 | 12 | 40.2 | 1.0 | 0.4 |
| Example 31 | 13 | 48.7 | 1.6 | 0.5 |
| Example 32 | 14 | 39.1 | 1.4 | 1.0 |
| Example 33 | 15 | 40.3 | 1.5 | 1.0 |
| Example 34 | 16 | 38.9 | 1.0 | 0.5 |
| Example 35 | 17 | 47.1 | 1.6 | 0.4 |
| Example 36 | 8 | 46.0 | 1.6 | 0.5 |
| Example 37 | 9 | 45.4 | 1.0 | 0.5 |
| Example 38 | 8 | 65.1 | 2.4 | 1.0 |
| Example 39 | 8 | 66.3 | 2.5 | 1.0 |
| Reference 6 | | 3.2 | 1.0 | 0.5 |
| Reference 7 | | 36.7 | 1.7 | 1.0 |
| Reference 8 | | 32.1 | 1.6 | 1.0 |

4,4'-BPA: 2,2-bis(4'-hydroxyphenyl)propane,
2,4'-BPA: 2-(2'-hydroxyphenyl)-2-(4'-hydroxyphenyl)propane (isomer),
COD: 2,2,4-trimethyl-4-(4'-hydroxyphenyl)chroman (by-product of reaction)

What is claimed is:

1. A process for preparing bisphenol A which comprises reacting phenol with acetone in the presence of an acid and a polyorganosiloxane having a mercapto group-containing hydrocarbon group.

2. A process in accordance with claim 1, wherein said acid and said polyorganosiloxane having a mercapto group-containing hydrocarbon group comprise a polyorganosiloxane having both a mercapto group-containing hydrocarbon group and a sulfonic acid group.

3. A process in accordance with claim 2, wherein said sulfonic acid group comprises an aromatic sulfonic acid group.

4. A process in accordance with claim 2, wherein said sulfonic acid group comprises an alkylsulfonic acid group.

5. A process in accordance with claim 1, wherein said mercapto group-containing hydrocarbon group comprises at least one selected from the group consisting of mercaptomethyl group, 2-mercaptoethyl group, 3-mercapto-n-propyl group, 4-mercaptophenyl group, and 4-mercaptomethylphenyl group.

6. A process in accordance with claim 2, wherein said mercapto group-containing hydrocarbon group comprises at least one selected from the group consisting of mercaptomethyl group, 2-mercaptoethyl group, 3-mercapto-n-propyl group, 4-mercaptophenyl group, and 4-mercaptomethylphenyl group.

7. A process in accordance with claim 3, wherein said mercapto group-containing hydrocarbon group comprises at least one selected from the group consisting of mercaptomethyl group, 2-mercaptoethyl group, 3-mercapto-n-propyl group, 4-mercaptophenyl group, and 4-mercaptomethylphenyl group.

8. A process in accordance with claim 4, wherein said mercapto group-containing hydrocarbon group comprises at least one selected from the group consisting of mercaptomethyl group, 2-mercaptoethyl group, 3-mercapto-n-propyl group, 4-mercaptophenyl group, and 4-mercaptomethylphenyl group.

9. A polyorganosiloxane having both a sulfonic acid group and a mercapto group-containing hydrocarbon group, said polyorganosiloxane being obtained by the following steps of:

hydrolyzing i) at least one silane compound expressed by the general formula of $X_nSi(R_1)_{4-n}$, where n is an integer of from 1 to 3; X is at least one selected from the group consisting of a chlorine atom, a bromine atom, an iodine atom, and an alkoxyl group; $R_1$ is at least one hydrocarbon group selected from the group consisting of 1 to 20 carbon atoms-containing hydrocarbon groups having at least one mercapto group (—SH), 6 to 20 carbon atoms-containing hydrocarbon groups having an aromatic group, 1 to 15 carbon atoms-containing alkyl groups having at least one halogen atom, 2 to 15 carbon atoms-containing olefinic hydrocarbon groups having at least one carbon-carbon unsaturated double bond, and 2 to 15 carbon atoms-containing hydrocarbon groups having at least one epoxy group; and Si represents a silicon atom or ii) a mixture of said at least one silane compound expressed by the general formula of $X_nSi(R_1)_{4-n}$ and at least one silane compound expressed by the general formula of $SiX_4$, where X is at least one selected from the group consisting of a chlorine atom, a bromine atom, an iodine atom, and an alkoxyl group; and Si represents a silicon atom to yield a polyorganosiloxane;

sulfonating said hydrocarbon group $R_1$ to yield a polyorganosiloxane having a sulfonic acid group;

silylating said sulfonic said group-containing polyorganosiloxane with at least one silane compound expressed by the general formula of $X_nSi(R_2)_{4-n}$, where n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom; and hydrolyzing said silylated polyorganosiloxane.

10. A polyorganosiloxane having both a sulfonic acid group and a mercapto group-containing hydrocarbon group in accordance with claim 9, wherein said polyorganosiloxane is obtained by hydrolyzing said mixture of said at least one silane compound expressed by the general formula of $X_nSi(R_1)_{4-n}$ and at least one silane compound expressed by the general formula of $SiX_4$.

11. A polyorganosiloxane having both a sulfonic acid group and a mercapto group-containing hydrocarbon group, said polyorganosiloxane being obtained by the following steps of:

silylating silica gel with at least one silane compound expressed by the general formula of $X_nSi(R_1)_{4-n}$ and hydrolyzing said silylated compound to yield a polyorganosiloxane, where n is an integer of from 1 to 3; X is at least one selected from the group consisting of a chlorine atom, a bromine atom, an iodine atom, and an alkoxyl group; $R_1$ is at least one hydrocarbon group selected from the group consisting of 1 to 20 carbon atoms-containing hydrocarbon groups having at least one mercapto group (—SH), 6 to 20 carbon atoms-containing hydrocarbon groups having an aromatic group, 1 to 15 carbon atoms-containing alkyl groups having at least one halogen atom, 2 to 15 carbon atoms-containing olefinic hydrocarbon groups having at least one carbon-carbon unsaturated double bond, and 2 to 15 carbon atoms-containing hydrocarbon groups having at least one epoxy group; and Si represents a silicon atom;

sulfonating said polyorganosiloxane to yield a polyorganosiloxane having a sulfonic acid group;

silylating said sulfonic acid group-containing polyorganosiloxane with at least one silane compound expressed by the general formula of $X_nSi(R_2)_{4-n}$, where n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 and having at least one mercapto group (—SH); and Si represents a silicon atom; and hydrolyzing said silylated polyorganosiloxane.

12. A process for preparing a polyorganosiloxane having both a sulfonic acid group and a mercapto group-containing hydrocarbon group, said process comprising the following steps of:

hydrolyzing i) at least one silane compound expressed by the general formula of $X_nSi(R_1)_{4-n}$, where n is an integer of from 1 to 3; X is at least one selected from the group consisting of a chlorine atom, a bromine atom, an iodine atom, and an alkoxyl group; $R_1$ is at least one hydrocarbon group selected from the group consisting of 1 to 20 carbon atoms-containing hydrocarbon groups having at least one mercapto group (—SH), 6 to 20 carbon atoms-containing hydrocarbon groups having an aromatic group, 1 to 15 carbon atoms-containing allcyl groups having at least one halogen atom, 2 to 15 carbon atoms-containing olefinic hydrocarbon groups having at least one carbon-carbon unsaturated double bond, and 2 to 15 carbon atoms-containing hydrocarbon groups having at least one epoxy group; and Si represents a silicon atom or ii) a mixture of said at least one silane compound expressed by the general formula of $X_nSi(R_1)_{4-n}$ and at least one silane compound expressed by the general formula of $SiX_4$, where X is at least one selected from the group consisting of a chlorine atom, a bromine atom, an iodine atom, and an alkoxyl group; and Si represents a silicon atom to yield a polyorganosiloxane;

sulfonating said hydrocarbon group $R_1$ to yield a polyorganosiloxane having a sulfonic acid group;

silylating said sulfonic said group-containing polyorganosiloxane with at least one silane compound expressed by the general formula of $X_nSi(R_2)_{4-n}$, where n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom; and hydrolyzing said silylated polyorganosiloxane.

13. A process in accordance with claim 12, wherein said polyorganosiloxane is obtained by hydrolyzing said mixture of said at least one silane compound expressed by the general formula of $X_nSi(R_1)_{4-n}$ and at least one silane compound expressed by the general formula of $SiX_4$.

14. A process for preparing a polyorganosiloxane having both a sulfonic acid group and a mercapto group-containing hydrocarbon group, said process comprising the following steps of:

silylating silica gel with at least one silane compound expressed by the general formula of $X_nSi(R_1)_{4-n}$ and hydrolyzing said silylated compound to yield a polyorganosiloxane, where n is an integer of from 1 to 3; X is at least one selected from the group consisting of a chlorine atom, a bromine atom, an iodine atom, and an alkoxyl group; $R_1$ is at least one hydrocarbon group selected from the group consisting of 1 to 20 carbon atoms-containing hydrocarbon groups having at least one mercapto group (—SH), 6 to 20 carbon atoms-containing hydrocarbon groups having an aromatic group, 1 to 15 carbon atoms-containing alkyl groups having at least one halogen atom, 2 to 15 carbon atoms-containing olefinic hydrocarbon groups having at least one carbon-carbon unsaturated double bond, and 2 to 15 carbon atoms-containing hydrocarbon groups having at least one epoxy group; and Si represents a silicon atom;

sulfonating said polyorganosiloxane to yield a polyorganosiloxane having a sulfonic acid group;

silylating said sulfonic acid group-containing polyorganosiloxane with at least one silane compound expressed by the general formula of $X_nSi(R_2)_{4-n}$, where n is an integer of from 1 to 3; X is at least one selected from the group consisting of a chlorine atom, a bromine atom, an iodine atom, and an alkoxyl group; $R_2$ is a hydrocarbon group containing carbon atoms of from 1 to 20 having at least one mercapto group (—SH); and Si represents a silicon atom; and hydrolyzing said silylated polyorganosiloxane.

* * * * *